United States Patent [19]

Patel

[11] 4,157,094

[45] Jun. 5, 1979

[54] CATHETER WITH IMPROVED BALLOON AND TIP ASSEMBLY

[75] Inventor: Bhupendra C. Patel, Elgin, Ill.

[73] Assignee: The Kendall Company, Boston, Mass.

[21] Appl. No.: 829,767

[22] Filed: Sep. 1, 1977

[51] Int. Cl.² ............................................ A61M 25/00
[52] U.S. Cl. ................................................ 128/349 B
[58] Field of Search ......... 128/246, 325, 344, 348–351

[56] References Cited

U.S. PATENT DOCUMENTS

| | | | |
|---|---|---|---|
| 3,547,126 | 12/1970 | Birtwell | 128/349 B |
| 4,055,187 | 10/1977 | Patel et al. | 128/349 B |

*Primary Examiner*—Dalton L. Truluck
*Attorney, Agent, or Firm*—Powell L. Sprunger

[57] ABSTRACT

A catheter comprising, an elongated shaft having a distal end, a main lumen, and an inflation lumen extending along the shaft. The catheter has a tip member having a tip portion, and an annular tongue extended proximally from the tip portion and having a proximal end portion bonded to the shaft in the lumen. The catheter has an annular balloon member of elastic material defining a cavity, with the balloon member being positioned over the tongue intermediate the shaft and the tip portion of the tip member.

9 Claims, 3 Drawing Figures

U.S. Patent        Jun. 5, 1979        4,157,094
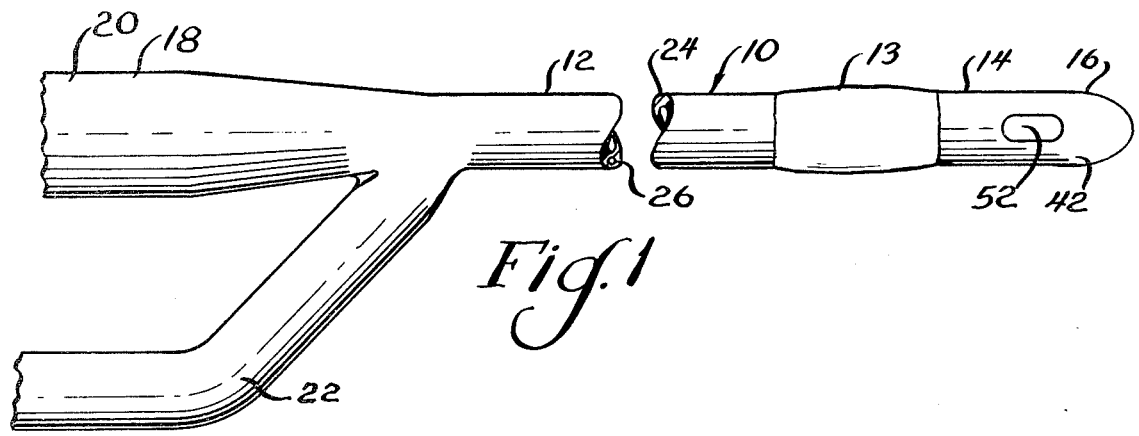
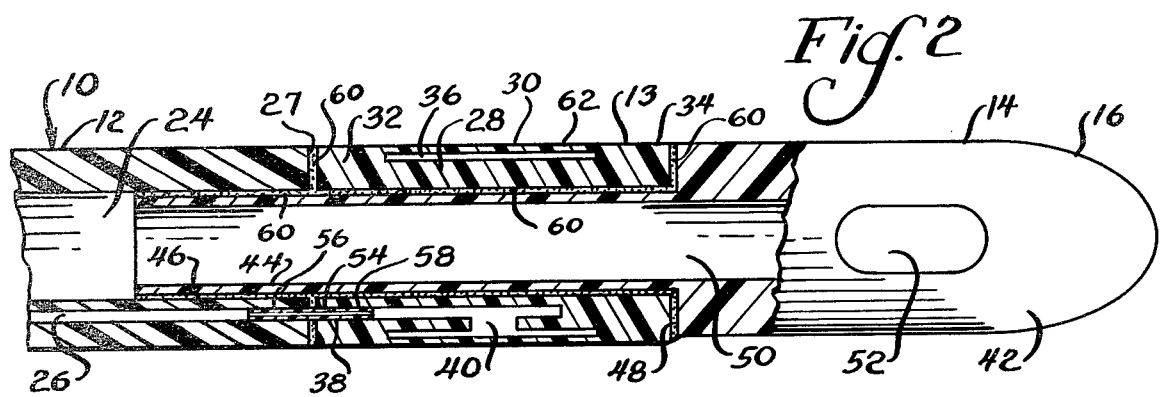
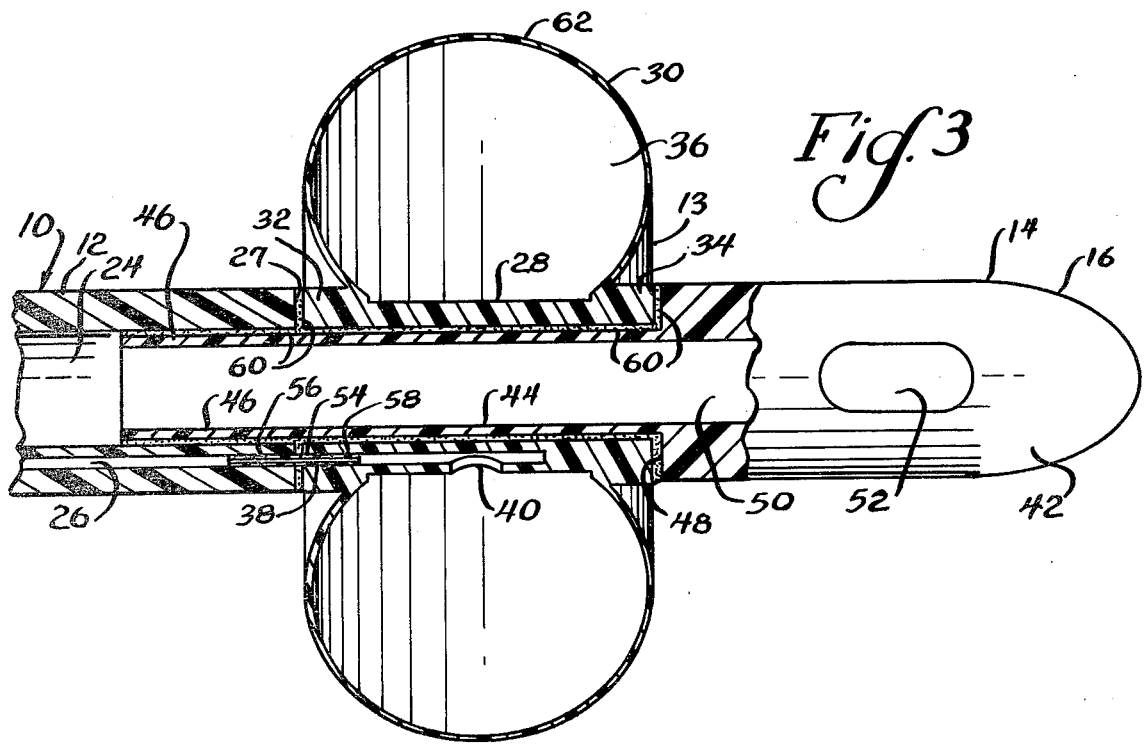

CATHETER WITH IMPROVED BALLOON AND TIP ASSEMBLY

BACKGROUND OF THE INVENTION

The present invention relates to catheters, and more particularly to balloon and tip assemblies for such catheters.

In the past, a various assortment of catheters, such as Foley catheters and endotracheal tubes, have been proposed for use in patients. In the case of urinary catheters, a conventional Foley catheter is normally constructed having a shaft defining a drainage lumen extending from a drainage eye adjacent a distal end of the catheter and an inflation lumen in a wall of the shaft, and having an expansible balloon overlying a distal portion of the shaft and defining a cavity communicating with the inflation lumen. In use, the distal end of the catheter is passed through the urethra until the drainage eye and balloon are located in the patient's bladder, and the balloon is inflated in the bladder to retain the catheter in the patient with a proximal end of the catheter located outside the patient's body. During catheterization, urine passes from the bladder through the drainage eye and lumen, and from the catheter through a drainage tube to a bag for collection therein.

A great majority of Foley catheters have been made from latex rubber through dipping techniques known to the art. However, a number of problems have been encountered with conventional latex catheters, particularly delamination of the catheter shaft causing blockage in the inflation lumen. Accordingly, there has been a desire to construct catheters from materials which display superior properties both from the view of improved performance during use and permitting simplified manufacture to reduce cost. For example, it is preferred that the catheter shaft be made from a material which can be extruded in order to facilitate the manufacturing process and eliminate the delamination problems in the shaft associated with dipped latex catheters. Additionally, the materials of the catheter shaft must be compatible with the patient's body to prevent deleterious results during use. The shaft, although flexible, should also have sufficient rigidity to permit placement of the catheter and prevent collapse of the shaft side walls. The balloon, of course, should be flexible and elastic to permit inflation in the patient's bladder, and preferably has a sufficient memory to assume its initial deflated configuration against the catheter shaft while being removed from the patient.

Unfortunately, many of the materials which display excellent properties when used for the catheter shaft are not suitable as a balloon, and vice versa. Hence, in many cases it is necessary to use dissimilar materials for the balloon and shaft which has created serious difficulties in joining the balloon and shaft together. Although it is often relatively simple to obtain a satisfactory bond between the balloon and shaft when the same material is used for both, known bonding techniques such as adhesive or heat sealing often do not provide sufficient strength between the balloon and shaft when dissimilar materials are used. For example, porous polytetrafluoroethylene provides an excellent candidate for the catheter shaft, but has been found unsatisfactory as the catheter balloon. Accordingly, attempts have been made to bond balloons made of suitable materials, such as silicone and latex, to such a shaft, and satisfactory bonds are only obtained with extreme difficulty which unduly complicates manufacture of the catheters.

SUMMARY OF THE INVENTION

A principal feature of the present invention is the provision of a catheter having an improved balloon and tip assembly.

The catheter of the present invention comprises, an elongated shaft having a distal end defining an annular shoulder, a main lumen extending through the shaft, and an inflation lumen in a wall of the shaft. The catheter has an annular balloon member of elastic material having inner and outer walls joined at opposed ends of the balloon member and defining a cavity intermediate the walls. The balloon member has a passageway communicating between the cavity and a proximal end of the balloon member, with the balloon member having inner dimensions approximately equal to the inner dimensions of the shaft and having a thickness approximately equal to the thickness of the shaft. The catheter has a tip member having a tip portion defining a distal end of the catheter and an annular tongue extending proximally from the tip portion. The tongue is longer than the balloon member and has outer dimensions approximately equal to the inner dimensions of the shaft. The tip member has a proximally facing shoulder at the juncture of the tip portion and the tongue, and a lumen extending through the tongue and at least a part of the tip portion. The tip portion has an opening communicating with the tip member lumen. The balloon member is bonded to the tongue with a distal end of the balloon member being located adjacent the tip member shoulder, with the tongue passing through the balloon member, and with a proximal end portion of the tongue extending proximally from the balloon member. The proximal portion of the tongue is received in the shaft lumen and is bonded to the shaft with the proximal end of the balloon member located adjacent the shaft shoulder. The catheter also has means for establishing communication between the inflation lumen and the balloon member passageway.

A feature of the present invention is that the catheter may be constructed in a simplified manner by bonding the balloon member to the tip member tongue, and by bonding the proximal end of the tongue to the shaft.

Another feature of the invention is that the balloon member is firmly bonded to the tip member and shaft, and is retained intermediate the shaft and the distal tip portion of the tip member.

Thus, another feature of the invention is that the catheter may be made in a simplified manner while obtaining a firm bond of the balloon member onto the catheter.

Yet another feature of the invention is that dissimilar materials may be used for the catheter shaft and the balloon member resulting in a catheter having improved characteristics.

Further features will become more fully apparent in the following description of the embodiments of this invention and from the appended claims.

DESCRIPTION OF THE DRAWINGS

In the drawings:

FIG. 1 is a fragmentary elevational view of a catheter of the present invention;

FIG. 2 is a fragmentary elevational view, taken partly in section, of the catheter of FIG. 1; and FIG. 3 is a fragmentary elevational view, taken partly in section, of the catheter of FIG. 2 illustrating a balloon member of the catheter as inflated.

DESCRIPTION OF THE PREFERRED EMBODIMENTS

Referring now to FIG. 1, there is shown a catheter generally designated 10 having an elongated shaft 12, an annular balloon member 13 of elastic material, a tip member 14 defining a distal end 16 of the catheter 10, a connector 18 at a proximal end 20 of the catheter, and a sidearm 22 extending from the shaft 12 or connector 18. As shown in FIGS. 1 and 2, the shaft 12 has a main lumen 24 extending through the shaft, an inflation lumen 26 extending through a wall of the shaft 12 and the sidearm 22, and a shoulder 27 at a distal end of the shaft. The shaft may be made of any suitable material, such as silicone, polyviny chloride, polyethylene, or Kraton, a trademark of Shell Oil Company, and, in a preferred form, is extruded. Although the catheter will be described in the form of a Foley catheter, it will be understood that the principals of the present invention may be utilized in connection with any suitable catheter, such as an endotracheal tube.

With reference to FIG. 2, the balloon member 13 has an inner wall 28 defining an inner surface of the balloon member, and an outer wall 30 defining an outer surface of the balloon member, with the inner and outer walls 28 and 30 being joined at proximal and distal ends 32 and 34, respectively, of the balloon member. The balloon member has a cavity 36 defined intermediate the inner and outer walls 28 and 30, and a passageway 38 extending from the proximal end 32 of the balloon member through the inner wall 28 to a location beneath the cavity 36, with the passageway 38 communicating with the cavity 36 through an opening 40. As shown, the balloon member 13 has inner dimensions approximately equal to the inner dimensions of the shaft 12, and has a thickness approximately equal to the thickness of the shaft. The balloon member 13 may be made of any suitable material, and, in a preferred form, is of one-piece construction. Thus, the balloon member may be made through dipping techniques of a latex rubber, or may be molded in a suitable manner.

The tip member 14 has a tip portion 42 defining the distal end 16 of the catheter, and an annular tongue 44 extending proximally from the tip portion 42. As shown, the tongue 44 has outer dimensions approximately equal to the inner dimensions of the catheter shaft 12 and the balloon member 13, and has a length greater than the length of the balloon member. Thus, the tongue 44 extends through the balloon member 13, and has a proximal end portion 46 extending proximally from the balloon member 13 and received in the shaft lumen 24. The tip member 14 also has a proximally facing shoulder 48 at the juncture of the tip portion 42 and the tongue 44. The tip member 14 has a lumen 50 extending through the tongue 44 and a part of the tip portion 42, with the tip portion 42 having a drainage eye or opening 52 communicating with the tip member lumen 50. The tip member 14 may be made of any suitable material, such as silicone, polyethylene, polyvinyl chloride, or Kraton, a trademark of Shell Oil Company. However, in a preferred form, the tip member 14 is made from the same material as the material of the shaft 12 in order to facilitate bonding of the tip member tongue 44 to the shaft 12. In a particularly desirable structure of the catheter, the catheter shaft is extruded, and the tip member 14 is moled in order to simplify the manufacturing techniques and reduce the cost of the catheter.

The catheter 10 also has a thin tubular section 54 having a proximal end 56 received in the inflation lumen 26 of the catheter shaft, and a distal end 58 received in the passageway 38 of the balloon member 13. In this manner, communication is established between the inflation lumen 26 and the balloon member cavity 36 through the tubular section 54, the passageway 3, and the opening 40.

The catheter may be manufactured in a simplified manner as follows. The outer surface of the tip member tongue 44 and shoulder 48 may be coated with a suitable bonding agent 60, such as adhesive, and the tongue 44 may be passed through the balloon member 13 until the distal end 34 of the balloon member 13 is located adjacent the shoulder 48 of the tip member 14. Next, the tubular section 54 is inserted into the passageway 38 of the balloon member 13. Finally, the proximal end portion 46 of the tongue 44 is inserted into the shaft lumen 24 while positioning the proximal end 56 of the tubular section 54 in the inflation lumen 26. If desired, additional adhesive may be applied during the latter manufacturing steps in order to obtain the desired bond between the proximal end portion 46 of the tongue 44 and the catheter shaft, and to locate adhesive between the shaft shoulder 27 and the proximal end 32 of the balloon member 13. As constructed, the balloon member 13 overlies a distal portion of the tip member tongue 44, and is located between the shoulers 27 and 48 of the catheter shaft 12 and the tip member 14. The balloon member 13 thus becomes bonded to both the tongue 44 and the shoulders of the catheter shaft 12 and tip member 14. In addition, the proximal end portion 46 of the tongue 44 is bonded to the inner surface of the catheter shaft at its distal end. Thus, the balloon member is firmly bonded and retained in place on the catheter even though dissimilar materials are used for the balloon member and the remaining portion of the catheter.

In use of the catheter, the catheter shaft 12 is passed through the patient's urethra, until the balloon member 13 is located in the patient's bladder. Next, a syringe is connected to a valve (not shown) on the catheter sidearm 22, and fluid is pumped by the syringe through the inflation lumen 26 into the cavity 36 of the balloon member 13 in order to inflate a central balloon portion 62 of the balloon member outer wall 30. In this manner, the catheter is retained in place, and urine drains through the drainage eye 52 and the lumens 50 and 24 of the tip member 14 and the catheter shaft 12 to a drainage tube (not shown) and a drainage bag (not shown) for collection of the urine therein.

The foregoing detailed description is given for clearness of understanding only, and no unnecessary limitations should be understood therefrom, as modifications will be obvious to those skilled in the art.

I claim:

1. A catheter, comprising:
    an elongated shaft having a distal end, a main lumen, and an inflation lumen extending along the shaft;
    a tip member having a tip portion defining a distal end of the catheter and a proximal shoulder, an annular tongue extending proximally from said tip portion shoulder and having a proximal end portion received in the main lumen of the shaft, said proximal tongue portion being bonded to the shaft with the shaft and tip member defining an annular groove recessed from an outer surface of the shaft intermediate the distal end of the shaft and said tip portion shoulder, said tip member having a lumen extending through said tongue, and an opening in said tip portion communicating with said lumen;

a separate annular balloon member positioned in said groove and overlying said tongue, said balloon member having outer and inner walls of elastic material joined at sides of the balloon member and defining a cavity, with a proximal side of said balloon member being located adjacent the distal end of said shaft, and with a distal side of said balloon member being located adjacent the tip portion shoulder; and means for establishing communication between the inflation lumen and said cavity to inflate said outer wall.

2. The catheter of claim 1 wherein the establishing means comprises a tubular section connected between the inflation lumen and said balloon member.

3. The catheter of claim 1 wherein said tip member has an annular shoulder at the juncture of the tip portion and said tongue, with said shoulder facing toward said balloon member.

4. The catheter of claim 1 wherein said balloon member has a passageway communicating between said cavity and a proximal end of the balloon member.

5. The catheter of claim 1 wherein said balloon member is of one-piece construction.

6. The catheter of claim 5 wherein said balloon member comprises a rubber material.

7. A catheter, comprising:

an elongated shaft having a distal end defining an annular shoulder, a main lumen extending through the shaft, and an inflation lumen in a wall of the shaft;

an annular balloon member of elastic material having inner and outer walls joined at opposed ends of the balloon member and defining a cavity intermediate said walls, and a passageway communicating between said cavity and a proximal end of the balloon member, said balloon member having inner dimensions approximately equal to the inner dimensions of the shaft and having a thickness approximately equal to the thickness of the shaft; and a tip member having a tip portion defining a distal end of the catheter and an annular tongue extending proximally from said tip portion, said tongue being longer than said balloon member and having outer dimensions approximately equal to the inner dimensions of said shaft, said tip member having a proximally facing shoulder at the juncture of said tip portion and tongue, and a lumen extending through said tongue and at least a part of said tip portion, and said tip portion having an opening communicating with said tip member lumen, said balloon member being bonded to said tongue with a distal end of the balloon member being located adjacent the tip member shoulder, with the tongue passing through the balloon member, and with a proximal end portion of the tongue extending proximally from the balloon member, said proximal end portion of the tongue being received in the shaft lumen and being bonded to the shaft with a proximal end of the balloon member being located adjacent the shaft shoulder; and means for establishing communication between the inflation lumen and the balloon member passageway.

8. The catheter of claim 7 wherein the establishing means comprises a tubular section having a first end received in the inflation lumen and a second end received in said passageway.

9. The catheter of claim 7 wherein said passageway extends partially through said inner wall of the balloon member beneath said cavity.

* * * * *